United States Patent
Rahman et al.

(10) Patent No.: US 8,577,474 B2
(45) Date of Patent: Nov. 5, 2013

(54) MINIMIZING INTERFERENCE BETWEEN CHARGING AND TELEMETRY COILS IN AN IMPLANTABLE MEDICAL DEVICE

(75) Inventors: Md. Mizanur Rahman, Stevenson Ranch, CA (US); Kiran Nimmagadda, Valencia, CA (US); Jordi Parramon, Valencia, CA (US); Emanuel Feldman, Simi Valley, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 899 days.

(21) Appl. No.: 12/616,178

(22) Filed: Nov. 11, 2009

(65) Prior Publication Data

US 2011/0112610 A1    May 12, 2011

(51) Int. Cl.
*A61N 1/372* (2006.01)
*A61N 1/378* (2006.01)

(52) U.S. Cl.
CPC .......... *A61N 1/37211* (2013.01); *A61N 1/3787* (2013.01)
USPC ............................................... 607/60; 607/61

(58) Field of Classification Search
USPC .................................. 607/30, 32–34, 59–61
See application file for complete search history.

(56) References Cited

U.S. PATENT DOCUMENTS

| | | | | |
|---|---|---|---|---|
| 4,561,443 | A * | 12/1985 | Hogrefe et al. | 607/31 |
| 5,713,939 | A * | 2/1998 | Nedungadi et al. | 607/33 |
| 5,735,887 | A | 4/1998 | Barreras, Sr. et al. | |
| 5,861,019 | A | 1/1999 | Sun et al. | |
| 6,516,227 | B1 | 2/2003 | Meadows et al. | |
| 6,701,188 | B2 * | 3/2004 | Stroebel et al. | 607/32 |
| 7,177,698 | B2 | 2/2007 | Klosterman et al. | |
| 7,209,792 | B1 * | 4/2007 | Parramon et al. | 607/120 |
| 7,212,110 | B1 * | 5/2007 | Martin et al. | 340/539.12 |
| 7,428,438 | B2 | 9/2008 | Parramon et al. | |
| 2003/0078634 | A1 * | 4/2003 | Schulman et al. | 607/61 |

(Continued)

FOREIGN PATENT DOCUMENTS

| | | |
|---|---|---|
| EP | 1598092 | 11/2005 |
| WO | 2008/048724 | 4/2008 |
| WO | 2009/061537 | 5/2009 |
| WO | 2009134466 | 11/2009 |

OTHER PUBLICATIONS

U.S. Appl. No. 12/117,487, filed May 8, 2008, Parramon et al.
U.S. Appl. No. 12/372,501, filed Feb. 17, 2009, Nimmagadda.

(Continued)

*Primary Examiner* — Carl H Layno
*Assistant Examiner* — Jessica Sarcione
(74) *Attorney, Agent, or Firm* — Wong, Cabello, Lutsch, Rutherford & Brucculeri, LLP.

(57) ABSTRACT

An improved implantable pulse generator (IPG) containing improved telemetry circuitry is disclosed. The IPG includes charging and telemetry coils within the IPG case, which increases their mutual inductance and potential to interfere with each other; particularly problematic is interference to the telemetry coil caused by the charging coil. To combat this, improved telemetry circuitry includes decoupling circuitry for decoupling the charging coil during periods of telemetry between the IPG and an external controller. Such decoupling circuitry can comprise use of pre-existing LSK circuitry during telemetry, or new discrete circuitry dedicated to decoupling. The decoupling circuitry is designed to prevent or at least reduce induced current flowing through the charging coil during data telemetry. The decoupling circuitry can be controlled by the microcontroller in the IPG, or can automatically decouple the charging coil at appropriate times to mitigate an induced current without instruction from the microcontroller.

31 Claims, 7 Drawing Sheets

(56) References Cited

U.S. PATENT DOCUMENTS

| | | |
|---|---|---|
| 2003/0171792 A1 | 9/2003 | Zarinetchi et al. |
| 2004/0082977 A1 | 4/2004 | Engmark et al. |
| 2005/0075693 A1* | 4/2005 | Toy et al. .................. 607/60 |
| 2005/0088357 A1 | 4/2005 | Hess et al. |
| 2005/0131496 A1 | 6/2005 | Parramon et al. |
| 2005/0244611 A1 | 11/2005 | Deininger et al. |
| 2008/0172109 A1 | 7/2008 | Rahman et al. |
| 2009/0024179 A1 | 1/2009 | Dronov |
| 2009/0069869 A1 | 3/2009 | Stouffer et al. |
| 2009/0228076 A1 | 9/2009 | Ameri |
| 2009/0270948 A1* | 10/2009 | Nghiem et al. ............. 607/60 |
| 2011/0046699 A1* | 2/2011 | Mazanec .................. 607/61 |

OTHER PUBLICATIONS

International Search Report and Written Opinion regarding corresponding application No. PCT/US2010/049215, dated Dec. 6, 2010.
International Search Report and Written Opinion regarding corresponding application No. PCT/US2010/049210, dated Nov. 30, 2010.
U.S. Appl. No. 11/215,946, filed Aug. 30, 2005, Yan et al.

\* cited by examiner

MINIMIZING INTERFERENCE BETWEEN CHARGING AND TELEMETRY COILS IN AN IMPLANTABLE MEDICAL DEVICE

FIELD OF THE INVENTION

The present invention relates to improved circuitry for an implantable medical device to minimize interference between the device's charging and telemetry coils.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIGS. 1A and 1B, a SCS system typically includes an Implantable Pulse Generator (IPG) 100, which includes a biocompatible device case 30 formed of a conductive material such as titanium for example. The case 30 typically holds the circuitry and battery 26 necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The leads 102, 104 couple to the IPG 100 using lead connectors 38a and 38b, which are fixed in a non-conductive header material 36, which can comprise an epoxy for example.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils (more generally, antennas) are generally present in the IPG 100: a telemetry coil 13 used to transmit/receive data to/from an external controller 12; and a charging coil 18 for charging or recharging the IPG's battery 26 using an external charger 50. The telemetry coil 13 is typically mounted within the header 36 of the IPG 100 as shown, and may be wrapped around a ferrite core 13'.

As just noted, an external controller 12, such as a hand-held programmer or a clinician's programmer, is used to wirelessly send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12. The communication of data to and from the external controller 12 is enabled by a coil (antenna) 17.

The external charger 50, also typically a hand-held device, is used to wirelessly convey power to the IPG 100, which power can be used to recharge the IPG's battery 26. The transfer of power from the external charger 50 is enabled by a coil (antenna) 17'. For the purpose of the basic explanation here, the external charger 50 is depicted as having a similar construction to the external controller 12, but in reality they will differ in accordance with their functionalities as one skilled in the art will appreciate.

Wireless data telemetry and power transfer between the external devices 12 and 50 and the IPG 100 takes place via inductive coupling, and specifically magnetic inductive coupling. To implement such functionality, both the IPG 100 and the external devices 12 and 50 have coils which act together as a pair. In case of the external controller 12, the relevant pair of coils comprises coil 17 from the controller and coil 13 from the IPG. In case of the external charger 50, the relevant pair of coils comprises coil 17' from the charger and coil 18 from the IPG.

When data is to be sent from the external controller 12 to the IPG 100 for example, coil 17 is energized with an alternating current (AC). Such energizing of the coil 17 to transfer data can occur using a Frequency Shift Keying (FSK) protocol for example, such as disclosed in U.S. patent application Ser. No. 11/780,369, filed Jul. 19, 2007. Energizing the coil 17 produces a magnetic field, which in turn induces a voltage in the IPG's coil 13, which produces a corresponding current signal when provided a closed loop path. This voltage and/or current signal can then be demodulated to recover the original data. Transmitting data from the IPG 100 to the external controller 12 occurs in essentially the same manner.

When power is to be transmitted from the external charger 50 to the IPG 100, coil 17' is again energized with an alternating current. Such energizing is generally of a constant frequency, and may be of a larger magnitude than that used during the transfer of data, but otherwise the basic physics involved are similar.

The IPG 100 can also communicate data back to the external charger 50 by modulating the impedance of the charging coil 18. This change in impedance is reflected back to coil 17' in the external charger 50, which demodulates the reflection to recover the transmitted data. This means of transmitting data from the IPG 100 to the external charger 50 is known as Load Shift Keying (LSK), and is useful to communicate data relevant during charging of the battery 26 in the IPG 100, such as the capacity of the battery, whether charging is complete and the external charger can cease, and other pertinent charging variables. LSK communication from an IPG 100 to an external charger is discussed further in U.S. patent application Ser. No. 12/354,406, filed Jan. 15, 2009.

As is well known, inductive transmission of data or power can occur transcutaneously, i.e., through the patient's tissue 25, making it particularly useful in a medical implantable device system. During the transmission of data or power, the coils 17 and 13, or 17' and 18, preferably lie in planes that are parallel, along collinear axes, and with the coils as close as possible to each other. Such an orientation between the coils 17 and 13 will generally improve the coupling between them, but deviation from ideal orientations can still result in suitably reliable data or power transfer.

The inventors consider certain aspects of the design of IPG 100 to be non-optimal. For one, the inventors find it unfortunate that the telemetry coil 13 resides in the IPG's header 36. The telemetry coil 13 takes up space in the header, which space is becoming more limited at IPG technology advances. It is desirable for patient comfort to continue to make IPGs 100 smaller, which shrinks header 36 volume accordingly. At the same time, future-generation IPGs are expected to offer even greater numbers of electrodes (e.g., 32, 64, etc). But accommodating an increased number of electrodes requires more space for lead connectors (see FIGS. 1A & 1B; 38a & 38b) in the header 36. As such, it is anticipated by the inventors that there may be little room left in the header for an adequate telemetry coil 13.

A solution to this problem is provided in this disclosure in the form of a new mechanical and/or electrical design for an IPG, or other implantable medical device.

DETAILED DESCRIPTION

The description that follows relates to use of the invention within a spinal cord stimulation (SCS) system. However, it is to be understood that the invention is not so limited, and could be used with any type of implantable medical device system.

An improved implantable pulse generator (IPG) containing improved telemetry circuitry is disclosed. The IPG includes charging and telemetry coils within the IPG case, which increases their mutual inductance and potential to interfere with each other; particularly problematic is interference to the telemetry coil caused by the charging coil. To combat this, improved telemetry circuitry includes decoupling circuitry for decoupling the charging coil during periods of telemetry between the IPG and an external controller. Such decoupling circuitry can comprise use of pre-existing LSK circuitry during telemetry, or new discrete circuitry dedicated to decoupling. The decoupling circuitry is designed to prevent or at least reduce induced current flowing through the charging coil during data telemetry. The decoupling circuitry can be controlled by the microcontroller in the IPG, or can automatically decouple the charging coil at appropriate times to mitigate an induced current without instruction from the microcontroller.

Figure 3A:
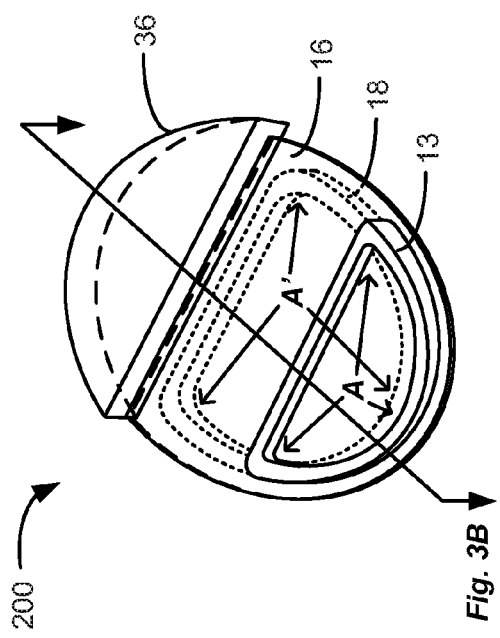
FIG. 3 shows an improved IPG in accordance with the invention, in which both the telemetry and charging coil are within the IPG case.
Figure 3B:
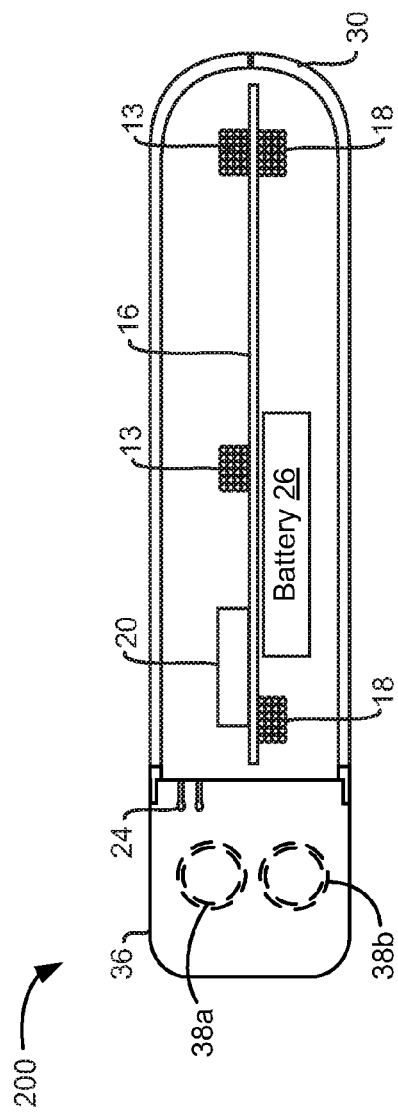

The inventors address the problem of reduced header 30 volume by placing the telemetry coil 13 inside the device case 30, as shown in FIGS. 3A and 3B, which shows the basic mechanical structure of the improved IPG 200. When the telemetry coil 13 is paced inside the case 30, more room is left in the header 36 for the at least one or more lead connectors, such as lead connectors 38a and 38b shown in FIG. 3B.

Figures 1A, 1B:
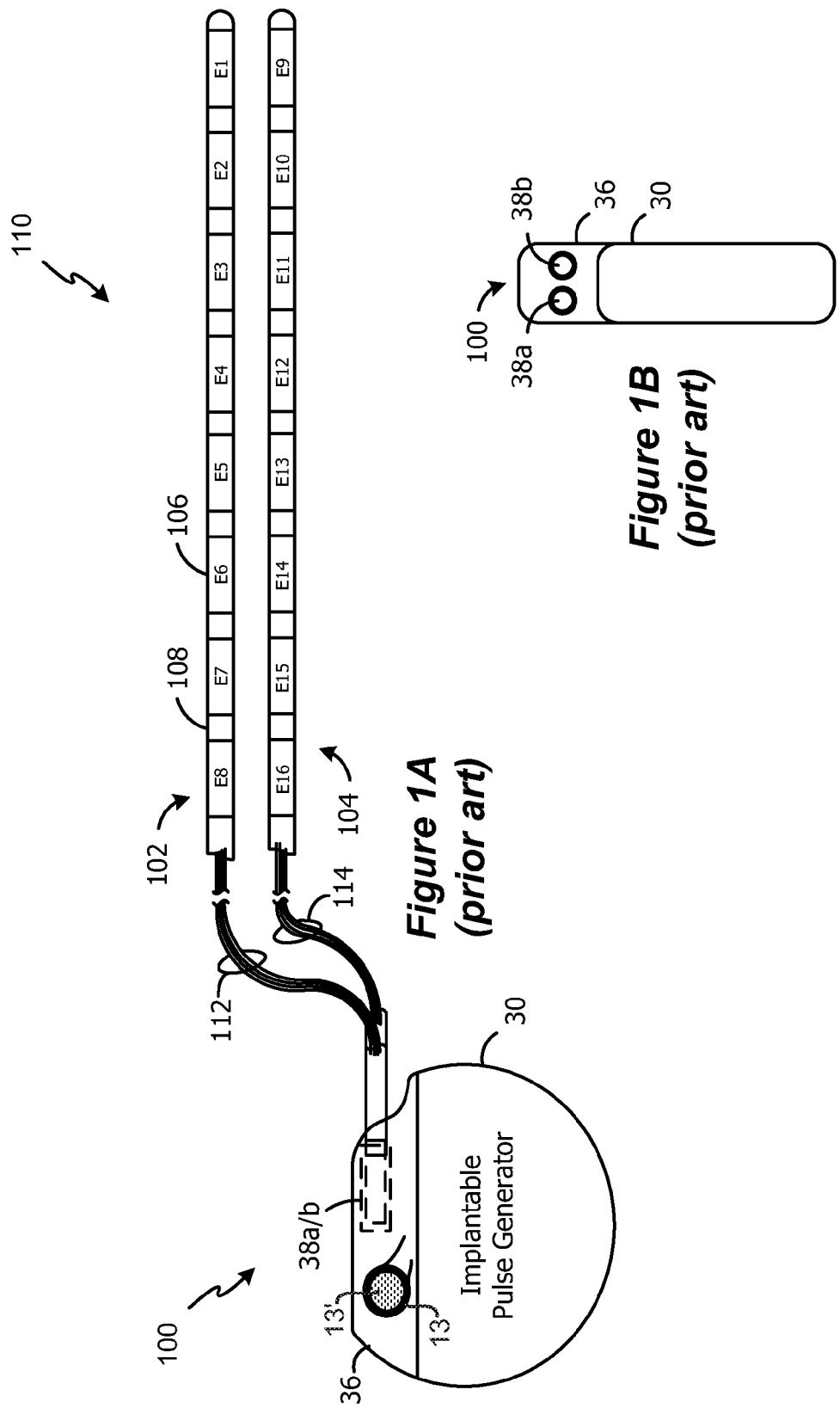
FIGS. 1A and 1B show an implantable medical device, and the manner in which an electrode array is coupled to the IPG in accordance with the prior art.
Figure 2:
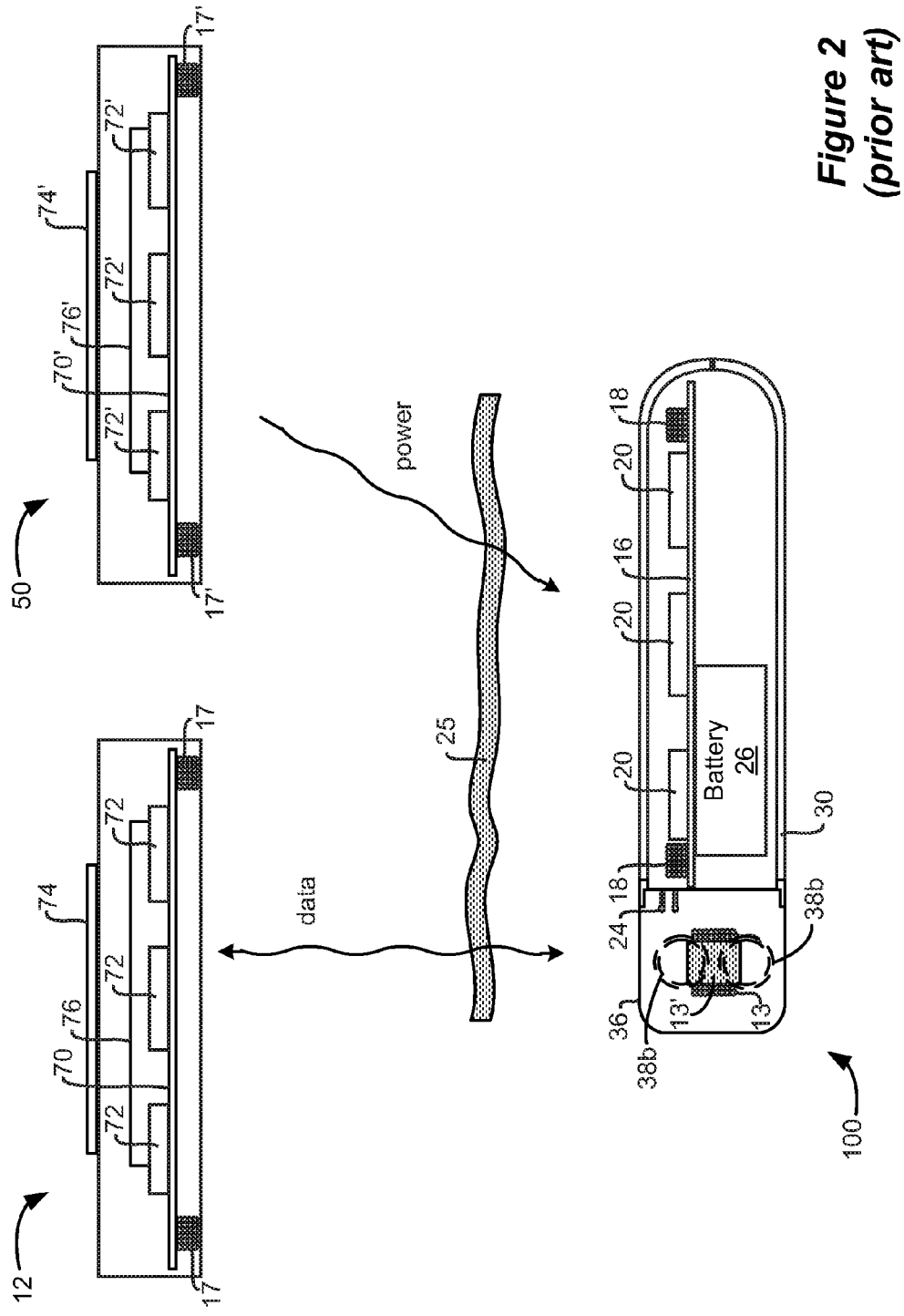
FIG. 2 shows the relation between the implantable medical device, an external controller, and an external charger.

Because the telemetry coil 13 is placed inside the device case 30, it will be shielded to some extent by the conductive material (e.g., titanium) from which the case is made. Such shielding attenuates data telemetry between the IPG 100 and the external controller 12, making such communications more difficult and less reliable. To counteract this, the telemetry coil 13 is preferably made to encompass a larger area A, as shown in FIG. 3A. This larger area improves coupling, and hence the reliability of data transfer, with the telemetry coil 17 in the external controller 12 (FIG. 2). A larger area also compensates for the lack of a ferrite core within the telemetry coil 13, which is eliminated because of its incompatibility with Magnetic Resonance Imaging (MRI) techniques. As shown, the charging coil 18 is proximate to one side of the circuit board 16, with the telemetry coil 13 proximate to the other side of the circuit board 16.

The charging coil 18 already present inside the device case 30 will interfere with the larger telemetry coil 13, and vice versa. To maximize power receipt from the external charger 50, the charging coil 18 is preferably made as large as possible inside the case 30, with the result that the area extent A encompassed by the telemetry coil 13 is, at least in part, overlapping or entirely within the area extent A' encompassed by the charging coil 18. As a result, the mutual inductance (coupling) between these two coils 13 and 18 is relatively high. This means that the coils 13 and 18 will load each other, which affects receipt of power or data at either coil. Of particular concern is interference of the charging coil 18 when data is being received at or transmitted by the telemetry coil 13. Because of the relatively high coupling, data received at or transmitted from the telemetry coil 13 will induce an opposing current, Ie, in coil 18. This induced current Ie in coil 18 comprises an unwanted energy sink, which effectively reduces the energy and hence reliably of the data transmission.

Figure 4:
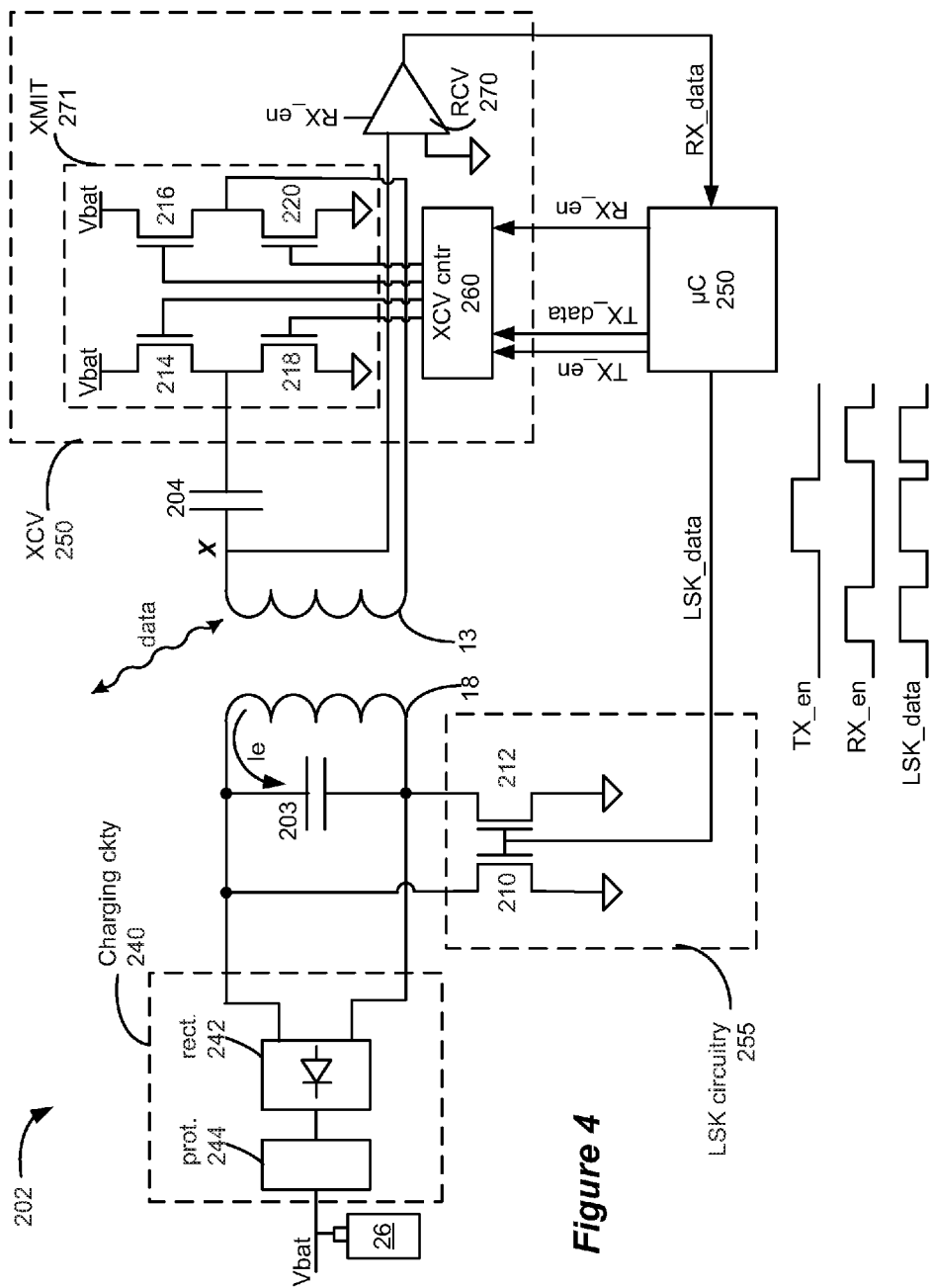
FIG. 4 shows a first embodiment of improved telemetry circuitry for the IPG of FIG. 3, in which the charging coil is decoupled from the telemetry coil using pre-existing LSK circuitry.

To combat this problem, the improved IPG 200 includes improved telemetry circuitry 202, one example of which is shown in FIG. 4. Charging coil 18 and capacitor 203 are shown in parallel, which comprise a resonant tank for receiving power from the external charger 50. This L-C circuit 18/203 is tuned to the frequency of the magnetic charging field output by the external charger 50, which may be 80 kHz or same as the data telemetry frequency as discussed below. Resonance of the L-C circuit in response to the magnetic charging field is sent to charging circuitry 240, which includes a rectifier 242 for converting the received power to a DC level, and protection circuitry 244 for controlling charging of the IPG battery 26 using the rectified power. In the example of FIG. 4, the input from the L-C circuit 18/203 to the charging circuitry 240 is differential, occurring at both ends of the paralleled circuit.

Also shown in FIG. 4 is telemetry coil 13 and capacitor 204, which comprise a resonant tank for receiving data from and transmitting data to the external controller 12. This L-C circuit is tuned to the frequency of the external controller 12, which may be 125 kHz or so. For example, when an FSK protocol is used, the frequency might be 121 kHz for transmission of a logic '0', and 129 kHz for a logic '1'. The L-C circuit 13/204 is coupled to transceiver circuitry 250, which includes a receiver 270 for receiving data from the external controller 12; transmission circuitry 271 for transmitting data back to the external controller 12; and transceiver control circuitry 260 coupled to the IPG 200's microcontroller 250.

Microcontroller 250 determines when it is appropriate to enable reception or transmission of data from or to the external controller 12 per conventional means, and issues reception and transmission enable signals RX_en or TX_en accordingly. When reception is enabled (RX_en), transceiver control circuitry 260 opens transistors 214 and 216 in transmission circuitry 271, and closes transistors 218 and 220. This connects telemetry coil 13 and capacitor 204 in parallel, with one node of the paralleled circuit being coupled to ground through transistors 218 and 220, and the other node X being input into receiver 270. As one skilled in the art will realize, receiver 270 conditions and demodulates the received signal to ultimately produce a digital received data signal, RX_data, which can be input to the microcontroller 250 for appropriate consideration. When transmission is enabled (TX_en), transceiver control circuitry 260 alternates between opening transistors 214 and 220 and closing transistors 216 and 218, and closing transistors 214 and 220 and opening transistors 216 and 218. This establishes a series connection between telemetry coil 13 and capacitor 204, with the alternating of the transistors switching the polarity of the current passing through the L-C circuit 13/204. The frequency of the alternation of the transistors is set by the data to be transmitted, TX_data, with the frequency set to 121 kHz for transmission of a logic '0', and 129 kHz for a logic '1', consistent with the above-illustrated FSK protocol.

As mentioned earlier, a potential problem with the arrangement of FIG. 4 is the mutual inductance between the telemetry coil 13 and the charging coil 18, a problem which is exacerbated when these coils are placed in proximity within the IPG case 30. In particular, when data is received at or transmitted from the telemetry coil 13, a current Ie is induced in the closed loop formed by the charging coil 18 and capacitor 203. This induced current Ie can be a significant power drain from the received or transmitted data signal, and so can affect the reliability of data transfer to or from the external controller 12. Moreover, the induced current Ie is enhanced by the somewhat close relationship between the frequency of the data (e.g., approximately 125 kHz) and the frequency at which the charging circuitry is tuned (e.g., 80 kHz).

In the example of FIG. 4, induced current Ie is reduced via novel control of LSK communication circuitry 255, although it bears noting that other embodiments to be discussed later remove or reduce Ie through means independent of the LSK circuitry. Prior to discussing such novel control of the LSK circuitry 255, such circuitry's normal use is discussed.

As mentioned in the Background, LSK circuitry can be used as a means of telemetering data back to the external charger 50 during charging, i.e., for sending data to the external charger when the charging coil receives power from the external charger. Such data is shown in FIG. 4 as LSK_data, which gates transistors 210 and 212. When LSK_data=1, transistors 210 and 212 are closed, and both ends of the paralleled L-C circuit 18/203 are shorted to ground. This modulates the load of the charging coil 18, causing reflections sensed at the external charger 50. The external charger 50 can then demodulate these reflections to recover the serial stream of LSK-transmitted data, as discussed previously.

In a traditional implementation, LSK circuitry 255 is disabled when the IPG is communicating with the external controller 12. That is, when microcontroller 250 asserts TX_en or RX_en, it disables LSK_data, which turns off transistors 210 and 212. This was logical in prior IPG implementations, because LSK circuitry 255 was only used for back telemetry to an external charger 50 during charging, and otherwise had no purpose or use during data telemetry with the external controller 12. Additionally, disabling of the LSK circuitry 255 in prior implementations was non-problematic because the telemetry coil 13 and charging coil 18 were not in proximity, and hence were relatively poorly coupled (see, e.g., FIG. 2).

By contrast, in the improved IPG 200, the LSK circuitry 255 is enabled during communications with the external controller 12 to mitigate the mutual inductance between the telemetry coil 13 and the charging coil 18. As already noted, mutual induction during data telemetry results in an induced current Ie in the charging coil 18 through the tuning capacitor 203, which siphons energy from telemetry—a problem exacerbated by the close proximity of the coils 13 and 18 in IPG 200's design (see, e.g., FIG. 3A). To combat this, and as shown in the timing diagrams at the bottom of FIG. 4, the LSK_data signal is asserted by the microcontroller 250 during data telemetry with the external controller 12, i.e., whenever TX_en or RX_en is asserted. Assertion of LSK_data, as mentioned before, will turn on transistors 210 and 212, thus grounding both ends of the paralleled L-C circuit 18/203. With both ends of the resonant circuitry grounded in this fashion, Ie in the charging coil 18 is reduced, which minimizes its loading on the telemetry coil 13, and improves the reliability of data transfer between the IPG 100 and the external controller 12.

How the induced current Ie is reduced can be understood as follows. The tuning capacitor 203 for L-C circuit 18/203 is chosen to create a resonance for the charging frequency (e.g., 80 kHz), which can be a frequency close to (or same) the telemetry frequency (e.g., 125 kHz). Induced current Ie will increase as the charging frequency approaches the telemetry frequency. When the LSK_data signal shorts the tuning capacitor 203, the L-C circuit is detuned to the coil 18's self-resonance frequency, which is usually much higher than the operating frequency. Even though the tuning capacitor 203 and the coil 18 are grounded at both of their ends, a voltage would still be induced across the coil 18 when a data telemetry field is present. However, because of the detuning caused by the shorted capacitor 203, the induced current Ie is significantly reduced. To remove Ie entirely to zero, one needs to open the closed loop formed by the L-C circuit 18/203, which is the approach taken in FIGS. 5, 6 and 7.

To summarize, in the improved IPG 200, the LSK_data signal is used to transmit serial data to the external charger 50 during charging, as is typical. Additionally, LSK_data is also used as a control signal to reduce loading of the telemetry coil 13 during data telemetry between the IPG 100 and the external controller 12. Using the preexisting LSK circuitry 255 to provide this benefit requires no change in the telemetry circuitry 202 other than to program the microcontroller 250 to assert LSK_data during periods of data telemetry. Of course, discrete logic gates could also be used to perform this function, and more than one control signal could be provided by the microcontroller 250 to the LSK circuitry 255. In any event, the implementation of the improved telemetry circuitry 202 shown in FIG. 4 improves the reliability of telemetry between the external controller 12 and the IPG 100 without substantial circuitry changes.

Although LSK_data is shown as enabled when transmission or reception are enabled (TX_en; RX_en), it should be understood that LSK_data can also be enabled when data is actually being transmitted from or received at the IPG 100

(e.g., TX_actual; RX_actual), instead of merely when it is enabled and waiting to do so without regard to whether data is actually being communicated.

Figure 5:
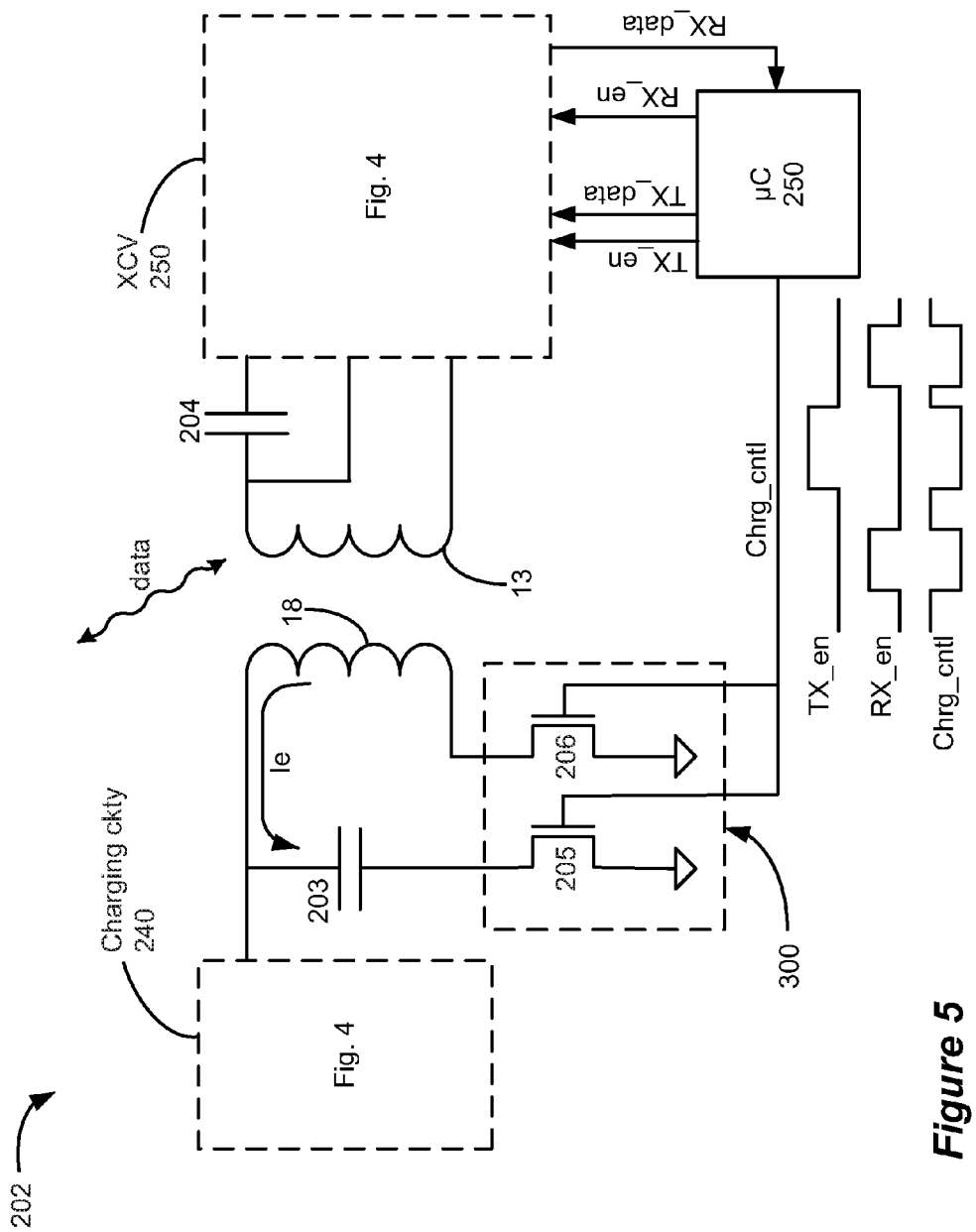
FIG. 5 shows a second embodiment of improved telemetry circuitry for the IPG of FIG. 3, which includes discrete decoupling circuitry for decoupling the charging coil from the telemetry coil.
Figure 6:
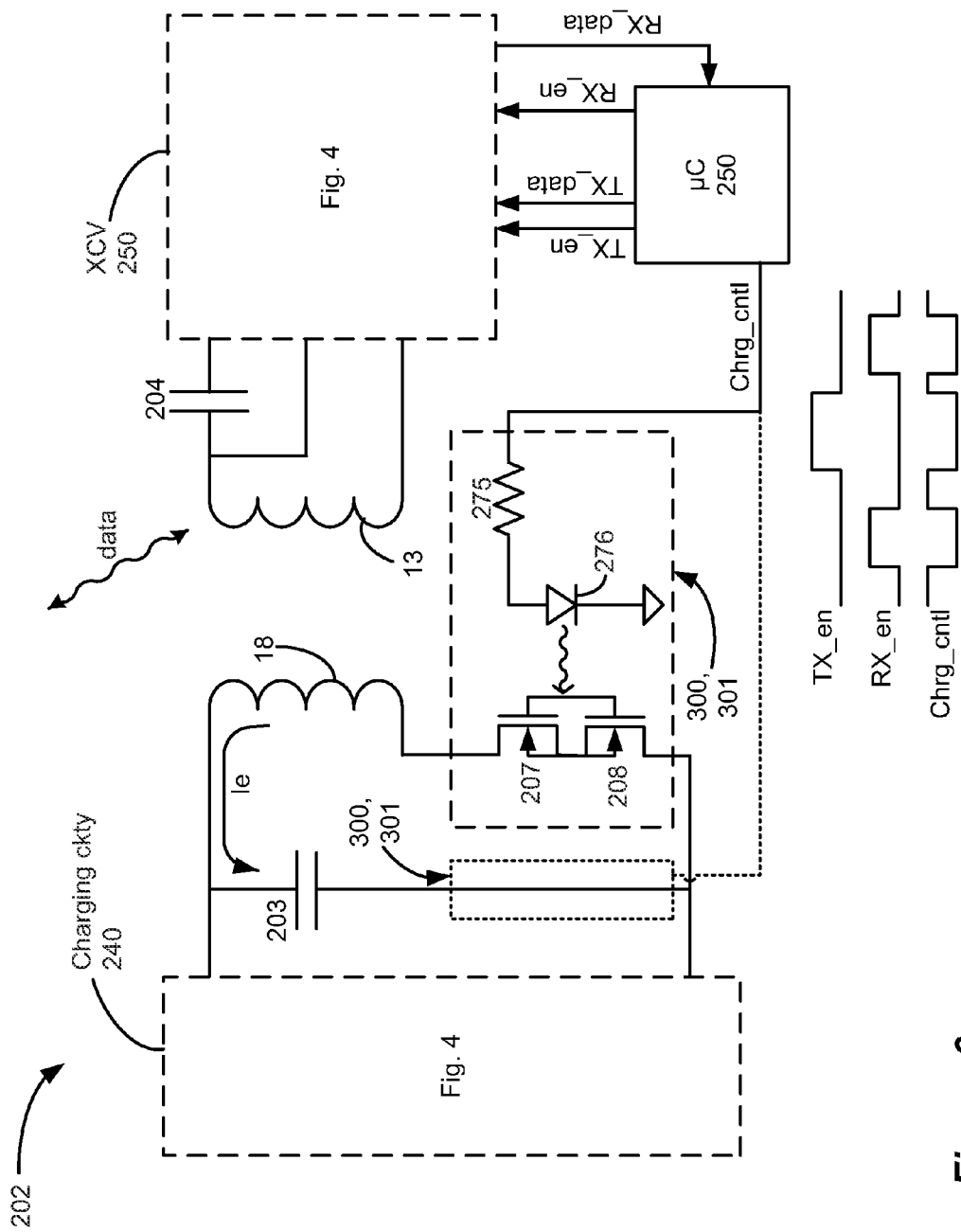
FIG. 6 shows a third embodiment of improved telemetry circuitry for the IPG of FIG. 3, which includes discrete decoupling circuitry for decoupling the charging coil from the telemetry coil.
Figure 7:
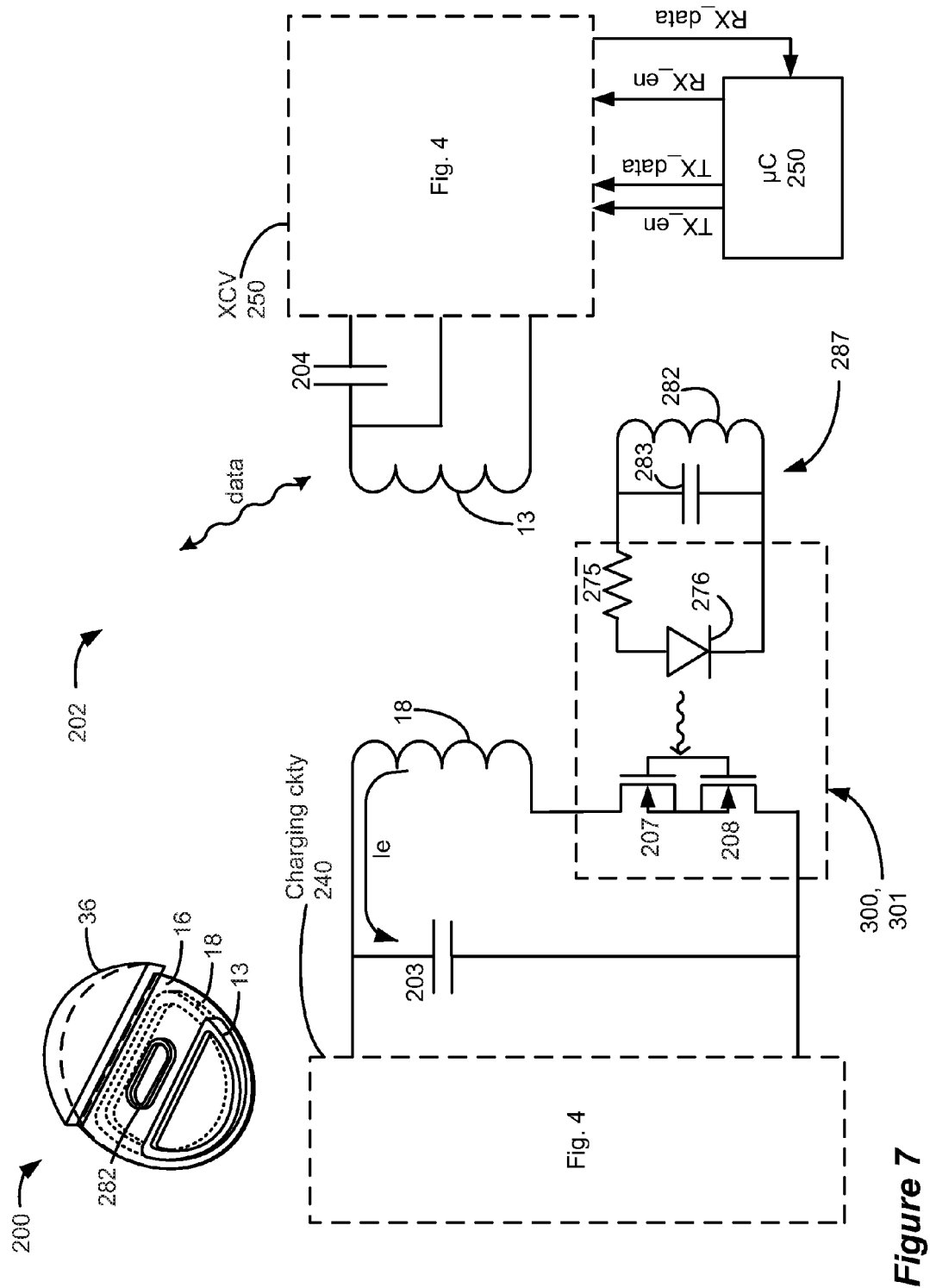
FIG. 7 shows a fourth embodiment of improved telemetry circuitry for the IPG of FIG. 3, which includes discrete decoupling circuitry for decoupling the charging coil from the telemetry coil which is not controlled by the IPG's microcontroller.

Not all implementations of the improved telemetry circuitry 202 require use of the pre-existing LSK circuitry 255, and FIGS. 5, 6, and 7 show additional implementations in which the LSK circuitry is not implicated (and thus not shown). The example of FIG. 5 includes decoupling circuitry 300 comprising two transistors 205 and 206. In this example, the paralleled resonant L-C circuit 18/203 provides only a single, non-differential input to the charging circuitry 240; the other end of the L-C circuit is coupled to ground during charging through transistors 205 and 206 by assertion of a charge control signal (Chrg_cntl=1). The Chrg_cntl control signal can be asserted either when a magnetic charging field is (or is expected to be) present, or simply could otherwise be asserted at all other times not involving data telemetry (i.e., whenever neither TX_en nor RX_en are asserted), as is shown in the timing diagrams at the bottom of FIG. 5. Back telemetry to the external charger 50 during charging may occur by the use of LSK circuitry, although such circuitry is not shown.

By contrast, during data telemetry with the external controller 12, i.e., when TX_en or RX_en are asserted, the charge control signal is deasserted (Chrg_cntl=0). This opens transistors 205 and 206 which opens the charging coil 18, which removes current flow through the charging coil 18, such that Ie=0, realizing the desirable benefits already discussed. Similar to FIG. 4, Chrg_cntl can also be deasserted when data is actually being transmitted from or received at the IPG 100 (e.g., TX_actual; RX_actual), instead of merely when it is enabled and waiting to do so.

Although decoupling circuitry 300 in FIG. 5 shows two transistors 205 and 206, it should be understood that only one transistor is needed to interrupt induced current Ie in the loop comprising L-C circuit 18/203.

The improved telemetry circuitry 202 of FIG. 6 also includes decoupling circuitry 300. The L-C circuit 18/203 is coupled in parallel, and provides a differential input to the charging circuitry 240. The decoupling circuitry 300 is connected in series with the coil 18, the decoupling capacitor 203, or both. In the embodiment shown, the decoupling circuitry 300 is shown in series with the coil 18, although the dotted lines show the optional provision of such circuitry in series with capacitor 203.

In this example, decoupling circuitry 300 can comprise an optical circuit, such as a PhotoMOS switch 301. A suitable PhotoMOS switch 301 for use in the improved telemetry circuitry 301 is manufactured by Panasonic Electric Works, Ltd. part number AQY221OOM. A data sheet for this device is submitted with this disclosure via an Information Disclosure Statement. Although familiarity with PhotoMOS switch 301 can be assumed, key internal circuitry within the switch 301 is shown in FIG. 6. When the charge control signal is asserted (Chrg_cntl=1), an LED 276 built into the PhotoMOS switch 301 turns on and emits radiation. This radiation is received by two serially-connected photo-sensitive MOS transistors 207 and 208. When illuminated by LED 276, these normally-off transistors 207 and 208 are turned on. In other words, transistors 207 and 208 are normally open, but become a short circuit when illuminated by the LED 276.

Thus, during charging or periods of no data telemetry (Chrg_cntl=1), the PhotoMOS switch 301 is closed, which couples the L-C circuit 18/203 to the charging circuitry 240 to enable power reception from the external charger 50. When charging is not enabled (Chrg_cntl=0), e.g., when TX_en or RX_en are asserted, the switch 301 is opened, which opens the L-C circuit loop 18/203, which removes induced current flow in charging coil 18 (Ie=0), realizing the desirable benefits already discussed. Similar to FIG. 5, Chrg_cntl can also be deasserted when data is actually being transmitted from or received at the IPG 100 (e.g., TX_actual; RX_actual), instead of merely when it is enabled and waiting to do so.

While the improved telemetry circuitry 202 of FIG. 6 features decoupling circuitry 300 using an optical solution, it should be appreciated that more standard solutions include the use of electrically-gated transistors could be used as well.

The embodiments of the improved telemetry circuit 202 shown so far rely on the provision of at least one control signals (LSK_data, Chrg_cntl) from the IPG's microcontroller 250 to decouple the charging coil 18 from the telemetry coil 13 during data telemetry with the external controller 12. However, this is not strictly required, and the charging circuitry can independently decide when it needs to be coupled or decoupled. For example, in FIG. 7, the decoupling circuitry 300 is able to independently detect the presence of the magnetic charging field and can enable the receipt of this power even without receipt of information from the microprocessor 250. For the rest of the time, including the data telemetry operation, the decoupling circuitry 300 disconnects the charge coil 18, thereby removing Ie by making Ie=0.

The improved telemetry circuit 202 of FIG. 7 is similar to that shown in FIG. 6, but adds a charge field detection circuit 287. The charge field detection circuit comprises an inductor 282 and a capacitor 283 in parallel and coupled to the inputs of the PhotoMOS switch 301. This L-C circuit 287 is tuned by appropriate choice of the values of the capacitor and inductor to resonate at the same frequency as the magnetic charging field broadcast by the external charger 50—approximately 80 kHz. The upper left corner of FIG. 7 shows one possible location for the inductor (coil) 282 used in the charge field detection circuit 287. Notice that coil 282 is preferably outside the area extent of telemetry coil 13 so as to prevent coupling between the two.

When a magnetic charging field has been broadcast from the external charger 50, L-C circuit 287 will detect this fact and start to resonate. Such resonance will power the diode 276 in the PhotoMOS switch 301 to radiate, which in turn will turn on transistors 207 and 208. Thus, the L-C tank 18/203 is coupled to the charging circuitry 240, and the implant's battery can be charged. By contrast, during other periods—during data telemetry at a different frequency (e.g., 125 kHz) or when no magnetic fields are present at all, L-C circuit 287 will not resonate, LED 276 will not radiate, and transistors 207 and 208 will be off. Importantly, the current Ie induced in the charging coil 18 equals zero during periods of data telemetry. This decouples the telemetry coil 13 from the charging coil 18, realizing the desirable benefits already discussed.

The disclosed embodiments of improved telemetry circuitry 202 assist in decoupling the telemetry coil 13 and the charging coil 18, which ultimately improves the reliability of data telemetry between the IPG 100 and the external controller 12. Such improved circuitry 202, as noted, is particularly useful when a relatively high coupling exists between the two coils 13 and 18, such as when the two coils are within the same IPG case 30, and encompass areas that are overlapping. However, this does not mean that all useful implementations are limited to these contexts.

While embodiments to this point have focused on interference of the charging coil 18 during data telemetry, it should be understood that mutual inductance between the charging coil 18 and the telemetry coil 13 can also result in interference of the telemetry coil 13 during charging. Therefore, although not shown, it should be understood that decoupling circuitry 200 could also be employed with telemetry coil 13, with the goal of preventing an induced current in that coil during the reception of a magnetic charging field at charging coil 18. Thus, decoupling circuitry can decouple the charging coil when the telemetry coil is communicating or enabled to communicate with the external controller, or can decouple the telemetry coil when the charging coil is receiving power or enabled to receive power form the external charger.

It should be noted that it is unimportant to implementations of the invention whether the IPG 100 functions with separate external devices (external controller 12 and external charger 50) for charging and data telemetry. Instead, a singular external device capable of both data telemetry and production of a charging filed could be used. See, e.g., U.S. patent application Ser. No. 12/368,385, filed Feb. 10, 2009.

Although the telemetry coil in the disclosed examples is capable of receiving and transmitting data from and to the external controller, other implementations will require only that the telemetry coil receive data, or that the telemetry coil transmit data. In recognition of this fact, and to cover each of the ideas using simple phrasing, a telemetry coil "receiving and/or transmitting data from and/or to the external controller" comprises a telemetry coil for receiving data from an external controller, or a telemetry coil for transmitting data to the external controller, or a telemetry coil for receiving and transmitting data from and to the external controller.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
    a charging coil for receiving power from an external charger;
    a telemetry coil for receiving and/or transmitting data from and/or to an external controller; and
    decoupling circuitry controllable to reduce or remove a current in the charging coil when receiving and/or transmitting data from and/or to the external controller.

2. The device of claim 1, wherein the device comprises a conductive case, and wherein the charging coil and telemetry coil are within the conductive case.

3. The device of claim 1, wherein the decoupling circuitry reduces the current by grounding both ends of the charging coil when receiving and/or transmitting data from and/or to the external controller.

4. The device of claim 1, wherein the decoupling circuitry removes the current by opening the charging coil.

5. The device of claim 1, wherein the decoupling circuitry comprises communication circuitry for sending data to the external charger when the charging coil receives power from the external charger.

6. The device of claim 1, further comprising a capacitor in parallel with the charging coil, and wherein the decoupling circuitry removes the current by opening a loop formed by the charging coil and the capacitor.

7. The device of claim 1, further comprising a microcontroller, wherein the microcontroller sends at least one control signal to control the decoupling circuitry.

8. The device of claim 7, wherein the microcontroller issues at least one first signal related to transmission and/or reception, and wherein the control signal is derived from the at least one first signal.

9. The device of claim 1, further comprising a microcontroller, wherein the decoupling circuitry functions independently without control from the microcontroller.

10. The device of claim 1, wherein the decoupling circuitry comprises optical circuitry.

11. An implantable medical device, comprising:
    a charging coil for receiving power from an external charger;
    a telemetry coil, wherein the telemetry coil can be enabled for the receipt and/or transmission of data from and/or to an external controller; and
    decoupling circuitry controllable to decouple the charging coil when the telemetry coil is enabled for the receipt and/or transmission of data from and/or to the external controller.

12. The device of claim 11, wherein the device comprises a conductive case, and wherein the charging coil and telemetry coil are within the conductive case.

13. The device of claim 11, wherein the decoupling circuitry grounds both ends of the charging coil when the telemetry coil is enabled for the receipt and/or transmission of data from and/or to an external controller.

14. The device of claim 11, wherein the decoupling circuitry opens the charging coil when the telemetry coil is enabled for the receipt and/or transmission of data from and/or to an external controller.

15. The device of claim 11, wherein the decoupling circuitry comprises communication circuitry for sending data to the external charger when the charging coil receives power from the external charger.

16. The device of claim 11, further comprising a capacitor in parallel with the charging coil, and wherein the decoupling circuitry opens a loop formed by the charging coil and the capacitor.

17. The device of claim 11, further comprising a microcontroller, wherein the microcontroller sends at least one control signal to control the decoupling circuitry.

18. The device of claim 11, further comprising a microcontroller, wherein the decoupling circuitry functions independently without control from the microcontroller.

19. The device of claim 11, wherein the decoupling circuitry comprises optical circuitry.

20. An implantable medical device, comprising:
    a charging coil for receiving a magnetic charging field from an external charger, wherein the received magnetic charging field is used to power the implantable medical device;
    a telemetry coil for receiving and/or transmitting data from and/or to an external controller; and
    decoupling circuitry controllable to couple the charging coil to the charging circuitry when receiving the magnetic charging field, but controllable to decouple the charging coil when not receiving the magnetic charging field.

21. The device of claim 20, wherein the decoupling circuitry decouples the charging coil by grounding both ends of the charging coil.

22. The device of claim 20, wherein the decoupling circuitry decouples the charging coil by opening the charging coil.

23. The device of claim 20, further comprising a capacitor in parallel with the charging coil, and wherein the decoupling circuitry decouples the charging coil by opening a loop formed by the charging coil and the capacitor.

24. The device of claim 20, further comprising a charge field detection circuit for detecting the magnetic charging field, and for controlling the decoupling circuitry.

25. An implantable medical device, comprising:
- a charging coil for receiving power from an external charger;
- a telemetry coil communicating with an external controller; and
- decoupling circuitry, wherein the decoupling circuitry is controllable to decouple the charging coil when the telemetry coil is communicating or enabled to communicate with the external controller, and is controllable to decouple the telemetry coil when the charging coil is receiving power or enabled to receive power from the external charger.

26. The device of claim 25, wherein the decoupling circuitry decouples the charging coil or the telemetry coil by grounding both ends of the charging coil or telemetry coil.

27. The device of claim 25 wherein the decoupling circuitry decouples the charging coil or the telemetry coil by opening the charging coil or telemetry coil.

28. An implantable medical device, comprising:
- a case;
- a charging coil within the case for receiving power from an external charger;
- a telemetry coil within the case a telemetry coil for receiving and/or transmitting data from and/or to an external controller; and
- decoupling circuitry controllable to reduce or remove a current in the charging coil when receiving and/or transmitting data from and/or to the external controller.

29. The device of claim 28, wherein the case is conductive.

30. The device of claim 28, further comprising a header comprising at least one lead connector for coupling to an electrode lead.

31. The device of claim 30, wherein the header is non-conductive.

* * * * *